(12) United States Patent
Feng et al.

(10) Patent No.: US 12,391,908 B2
(45) Date of Patent: Aug. 19, 2025

(54) REINFORCED GAS-PERMEABLE MEMBRANE AND REINFORCED GAS-PERMEABLE WELL UTILIZING SAME

(71) Applicant: Broadley-James Corporation, Irvine, CA (US)

(72) Inventors: Chang-Dong Feng, Long Beach, CA (US); Josh L. Rothman, Fallbrook, CA (US); Robert J. Garrahy, Laguna Niguel, CA (US); Scott T. Broadley, Laguna Beach, CA (US)

(73) Assignee: Broadley-James Corporation, Irvine, CA (US)

( * ) Notice: Subject to any disclaimer, the term of this patent is extended or adjusted under 35 U.S.C. 154(b) by 1208 days.

(21) Appl. No.: 16/353,823

(22) Filed: Mar. 14, 2019

(65) Prior Publication Data

US 2019/0284518 A1  Sep. 19, 2019

Related U.S. Application Data

(60) Provisional application No. 62/643,605, filed on Mar. 15, 2018.

(51) Int. Cl.
*C12M 1/04* (2006.01)
*A61M 39/18* (2006.01)
(Continued)

(52) U.S. Cl.
CPC ............ *C12M 23/24* (2013.01); *A61M 39/18* (2013.01); *B01D 65/003* (2013.01); *B01D 69/02* (2013.01);
(Continued)

(58) Field of Classification Search
None
See application file for complete search history.

(56) References Cited

U.S. PATENT DOCUMENTS 5,888,805 A * 3/1999 Endo .................. C12M 41/00
435/287.1
8,828,202 B2 * 9/2014 Feng .................. G01N 27/404
204/403.02

(Continued)

FOREIGN PATENT DOCUMENTS

DE        3029153 A1 *  3/1982 ........... B01D 53/228
WO  WO-2010148392 A1 * 12/2010 ............. C12M 41/34

OTHER PUBLICATIONS

POLYMERSnetBASE ("Polyethersulfone"). Accessed Oct. 23, 2021. https://poly.chemnetbase.com/faces/chemical/FullScreenEntry.xhtml?ide=%2FLMKwB%2FUB40%3D#2262 (Year: 2021).*

*Primary Examiner* — Michael A Marcheschi
*Assistant Examiner* — Nathan G Esperon
(74) *Attorney, Agent, or Firm* — Knobbe, Martens, Olson & Bear, LLP

(57) ABSTRACT

A gas-permeable well for use with a bioreactor may include a reinforced gas-permeable membrane. The gas-permeable membrane may include an integrated reinforcing structure such as a stainless steel mesh or perforated screen, and may include an integrated gasket or O-ring, or other regions of increased thickness. A sensor brought into close proximity to the reinforced gas-permeable membrane may take an indirect measurement of a condition of process medium on the other side of the gas-permeable membrane, such as a measurement of dissolved oxygen or carbon dioxide.

22 Claims, 7 Drawing Sheets

(51) Int. Cl.
  *B01D 65/00* (2006.01)
  *B01D 69/02* (2006.01)
  *B01D 69/10* (2006.01)
  *C12M 1/00* (2006.01)
  *C12M 1/32* (2006.01)
  *C12M 1/34* (2006.01)
  *C12M 3/00* (2006.01)
  *G01N 27/28* (2006.01)
  *G01N 33/497* (2006.01)

(52) U.S. Cl.
  CPC ......... *B01D 69/1071* (2022.08); *C12M 23/12* (2013.01); *C12M 23/14* (2013.01); *C12M 23/28* (2013.01); *C12M 23/42* (2013.01); *C12M 41/00* (2013.01); *C12M 41/34* (2013.01); *B01D 2313/025* (2013.01); *B01D 2313/041* (2022.08); *B01D 2313/042* (2022.08); *B01D 2325/24* (2013.01); *B01D 2325/40* (2013.01); *G01N 27/283* (2013.01); *G01N 33/4977* (2024.05)

(56) References Cited

U.S. PATENT DOCUMENTS

| | | | |
|---|---|---|---|
| 2004/0203140 A1* | 10/2004 | Akers | C12M 23/14 435/297.2 |
| 2011/0111489 A1* | 5/2011 | Beese | C12M 41/00 435/289.1 |
| 2012/0097557 A1* | 4/2012 | Baumfalk | C22B 19/30 206/216 |
| 2018/0010082 A1* | 1/2018 | Jaques | B01F 7/00375 |

* cited by examiner

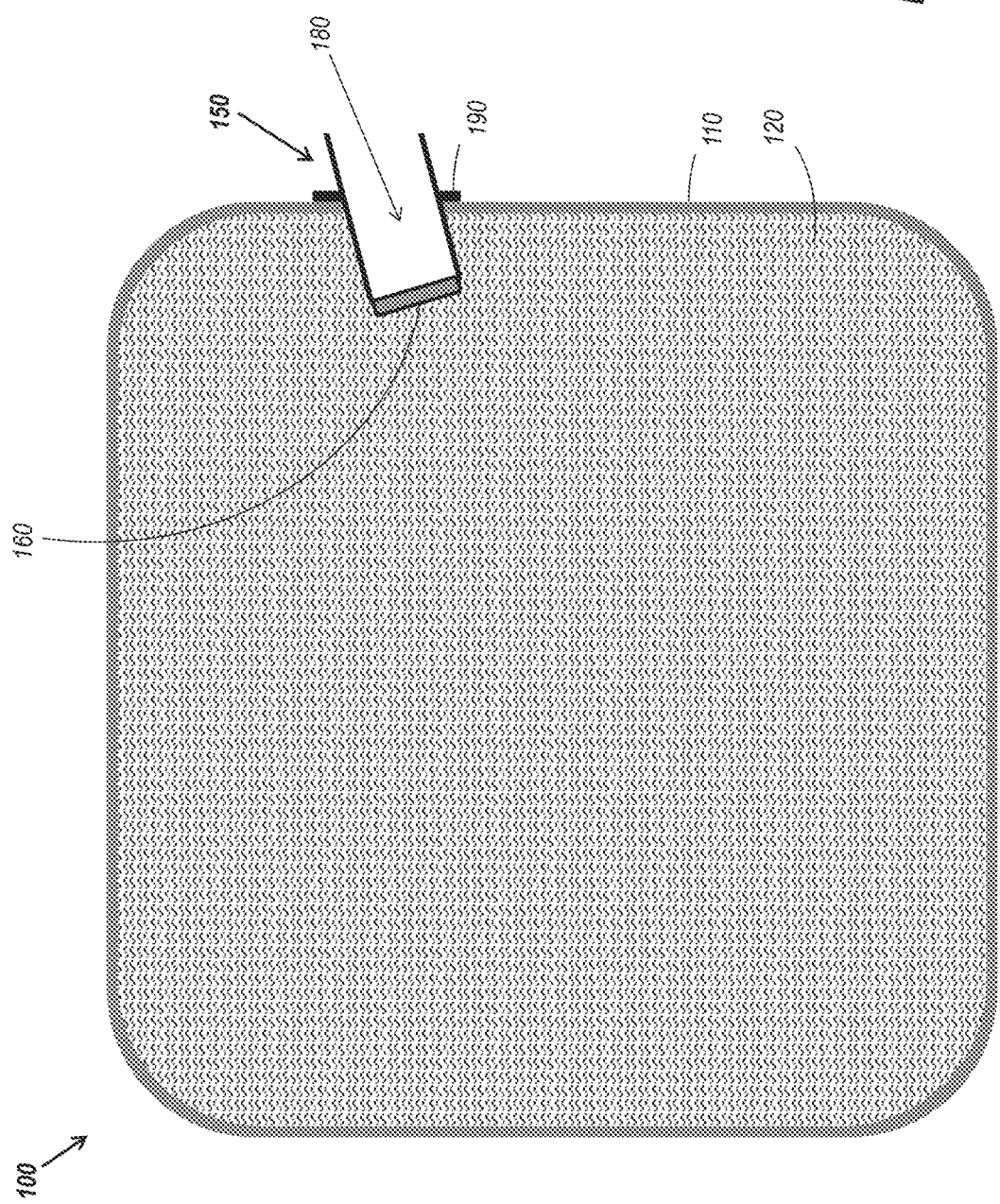

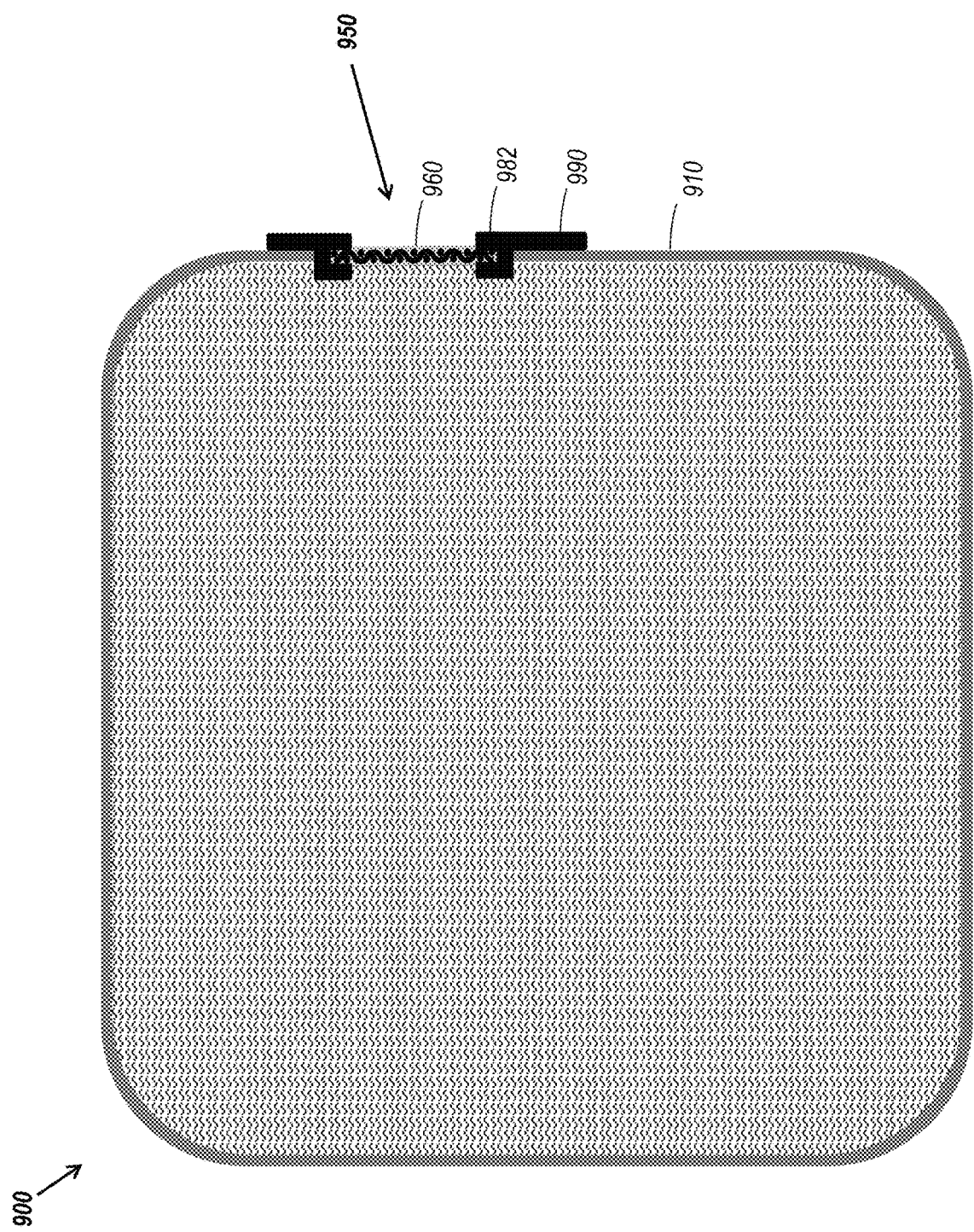

REINFORCED GAS-PERMEABLE MEMBRANE AND REINFORCED GAS-PERMEABLE WELL UTILIZING SAME

CROSS-REFERENCE TO RELATED APPLICATIONS

This application claims the benefit of U.S. Provisional Application No. 62/643,605, entitled REINFORCED GAS-PERMEABLE MEMBRANE AND REINFORCED GAS-PERMEABLE WELL UTILIZING SAME and filed on Mar. 15, 2018, which is hereby incorporated by reference in its entirety.

BACKGROUND

Technical Field

Embodiments described herein relate to sensor systems and associated components, and in particular are directed to gas-permeable wells into which sensors can be inserted, and gas-permeable reinforced membranes for use with the gas-permeable wells.

Description of the Related Art

In biopharmaceutical manufacturing processes, gas-permeable membranes can be used to allow indirect measurements to be taken of process media such as cell culture media within bioreactors, allowing measurements of the media using sensors such as dissolved oxygen (DO) sensors or carbon dioxide ($CO_2$) sensors without breaching the sterility of the bioreactor. However, when integrated into a bioreactor, these gas-permeable membranes represent a possible point of failure, and limit the pressure differential or other conditions to which the bioreactor can be exposed.

SUMMARY

In one aspect, a reinforced gas-permeable well for use with a bioreactor is provided, the reinforced gas-permeable well including a reinforced gas-permeable membrane, the reinforced gas-permeable membrane including a gas-permeable membrane, and a gas-impermeable reinforcing structure at least partially embedded within the gas-permeable membrane, the gas-impermeable reinforcing structure including at least one aperture extending therethrough, and a retaining structure configured to retain the gas-permeable membrane.

The gas-impermeable reinforcing structure can include an interwoven mesh. The gas-impermeable reinforcing structure can include a perforated screen. The gas-impermeable reinforcing structure can include a plurality of reinforcing elements extending across a central portion of the reinforced gas-permeable membrane.

The gas-impermeable reinforcing structure can further include a ring disposed at or near the periphery of the gas-impermeable reinforcing structure. The ring can be fully embedded within the gas-permeable membrane. The ring can be partially embedded within the gas-permeable membrane.

The gas-impermeable reinforcing structure can include stainless steel. The gas-permeable membrane can include silicone. The reinforced gas-permeable well can additionally include a sealing structure configured to allow the reinforced gas-permeable well to be installed in a wall of a bioreactor.

The reinforced gas-permeable well can additionally include a channel configured to receive a sensor therein, to allow the sensor to be positioned adjacent the reinforced gas-permeable membrane. The retaining structure can include at least one flange extending inwardly from the interior wall of the channel and configured to inhibit translation of the gas-permeable membrane in at least one direction along the channel. The reinforced gas permeable membrane can be oriented at an angle to an axis of the channel.

The reinforced gas-permeable well can be configured to be installed such that the reinforced gas-permeable membrane is positioned generally coplanar with a wall of the bioreactor. The reinforced gas-permeable membrane can be oriented at an angle to the sealing structure.

In one aspect, a bioreactor can include a reinforced gas-permeable well as described herein. The bioreactor can be a single-use bioreactor having flexible walls. The bioreactor can include an internal volume of greater than 2 liters or greater than 30 liters. The bioreactor can include a reusable bioreactor having rigid walls.

In another aspect, a reinforced gas-permeable well for use with a bioreactor is provided, the reinforced gas-permeable well including a reinforced gas-permeable membrane, the reinforced gas-permeable membrane including a reinforcing structure which decreases the permeability of the gas-permeable membrane in an area adjacent the reinforcing structure, and a retaining structure configured to retain the reinforced gas-permeable membrane.

The reinforcing structure can include at least one region of increased thickness. The at least one region of increased thickness can extend around the periphery of the reinforced gas-permeable membrane. The at least one region of increased thickness can include an integrated O-ring or gasket.

The reinforcing structure can include a gas-impermeable reinforcing structure at least partially embedded within the gas-permeable membrane and including at least one aperture extending therethrough. The gas-impermeable reinforcing structure can include an interwoven mesh. The gas-impermeable reinforcing structure can include a perforated screen. The gas-impermeable reinforcing structure can include a plurality of reinforcing elements extending across a central portion of the reinforced gas-permeable membrane.

BRIEF DESCRIPTION OF THE DRAWINGS

FIG. 1A is a side cross-sectional view schematically illustrating a bioreactor having an integrated gas-permeable well for sensor access.

FIG. 9 is a cross-sectional view schematically illustrating an embodiment of a bioreactor having a low-profile reinforced gas-permeable well installed therein, where the reinforced gas-permeable membrane substantially flush with the wall of the bioreactor.

DETAILED DESCRIPTION

Figure 1B:
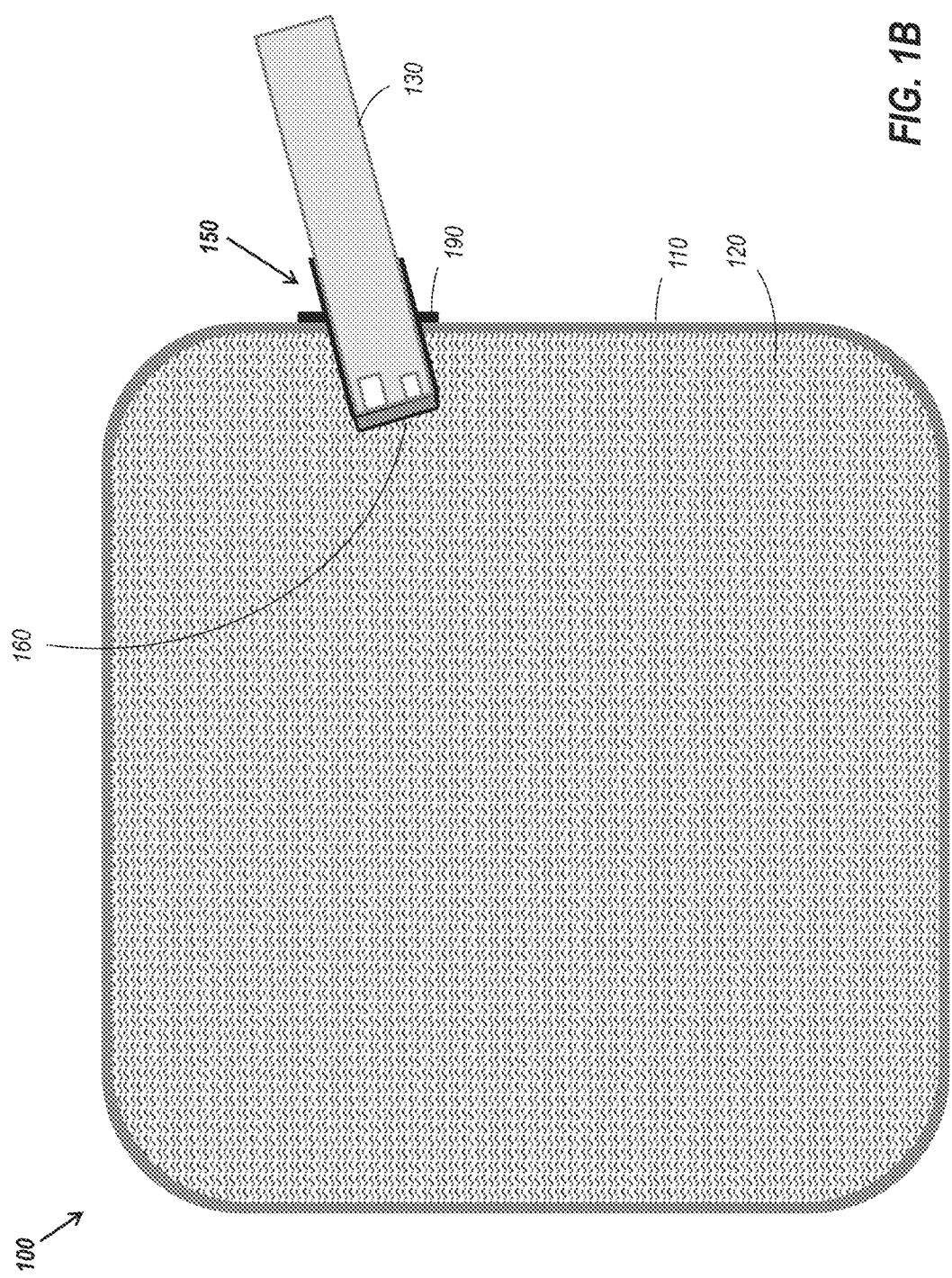
FIG. 1B is a side cross-sectional view schematically illustrating the bioreactor of FIG. 1A, with a dissolved oxygen sensor inserted into the gas-permeable well.

By using a gas-permeable membrane, indirect measurements of a process medium within a bioreactor or other container can be made. A dissolved oxygen (DO) sensor, $CO_2$ sensor, or similar sensor can be configured to provide a signal indicative of the parameter of the medium to be measured. For example, a DO sensor can generate a signal, depending on its sensing mechanism, where the signal indicative of the amount of oxygen in a process medium to which the sensor is exposed. However, indirect measurement of the medium is also possible, without direct contact between the sensor and the medium to be measured.

Due to diffusion of gas through a gas-permeable membrane, an accurate measurement of the oxygen content or other parameter of the medium can be obtained even when a sensor is not brought into direct contact with the medium. A sensing surface of a sensor such as a DO sensor can be brought adjacent or into contact with a gas-permeable membrane when a measurement is to be taken. The measurement taken will be indicative of conditions within the process medium despite the lack of actual contact between the process medium and the sensing surface of the sensor.

In some embodiments, the walls of a bioreactor may be rigid, and the bioreactor may be reusable, with sterilization occurring between uses of the bioreactor. In such embodiments, a sensor may be directly installed into or through a wall of a rigid bioreactor. The rigidity of the bioreactor wall can provide mechanical support for the installed sensor, which can remain sealed in place during sterilization of the bioreactor and subsequent use of the bioreactor.

In other embodiments, however, the bioreactor can include a bag or other flexible structure, which is filled with and retains the process medium. Flexible bioreactor bags may in some embodiments be single-use bioreactors, which can be disposed of rather than being re-sterilized and re-used. Such a flexible bioreactor may itself be seated within a rigid retaining vessel, but as the walls of the actual containment vessel retaining the process medium are flexible, sensors and other components can be configured to be insertable through ports in the bioreactor wall or may be installed within the bioreactor prior to sterilization and/or filling of the bioreactor with sterile components or media.

In other embodiments, certain sensors and other components may interact with a bioreactor which has already been sterilized or filled with process media. For example, sensors may be configured to be insertable into gas-permeable wells in the flexible bioreactor wall, such that the sterility and integrity of the flexible bioreactor are not compromised by the insertion of the sensor. In some embodiments, a gas-permeable well may be built into the flexible bioreactor bag or otherwise installed prior to the assembled bioreactor being sterilized or filled with a process medium. This allows a sensor to be freely inserted into the well and removed during the bioreactor process as needed, and does not require that the sensor be coupled to a single bioreactor for the duration of a process in that bioreactor. The freedom to insert and remove the sensor as desired also allows validation of the measurements, and reuse of a single sensor with multiple single-use bioreactors.

For indirect measurements, such as the measurement of dissolved oxygen through a gas-permeable membrane, which itself is a sterile barrier, the sensor itself need not be installed in the bioreactor during sterilization, shipment, and a setup process at the end-user's site. Thus, the sensor need not be installed during sterilization or prior to the deployment of the bioreactor bag. However, to maintain the sterility of the bioreactor bag, the gas-permeable well including a gas-permeable membrane must be installed in the bioreactor bag prior to the sterilization process and remain in place thereafter. Similarly, the gas-permeable membrane must remain in place after the bioreactor is deployed, and through the conclusion of the process, to maintain the integrity of the bioreactor.

FIG. 1A is a side cross-sectional view schematically illustrating a bioreactor having an integrated gas-permeable well for sensor access. The bioreactor 100 includes a wall 110 and a process medium 120 retained therein. A gas-permeable well 150 including a channel 180 dimensioned to accommodate a sensor (not shown) that extends inwardly from the wall 110 of the bioreactor 100 and is canted downward, terminating in a gas-permeable membrane 160.

The gas-permeable membrane 160 may include a thin layer of silicone, although other gas-permeable materials may also be used. The gas-permeable membrane 160 is sealed to the channel 180 of the well 150 to provide a fluid-tight seal, allowing certain gases to pass through the gas-permeable membrane while preventing leakage of the process medium 120 through or between the components of the well 150. In particular, gas-permeable membrane 160 can allow gases such as oxygen to diffuse through the membrane 160. Thus, the concentration of such gases in the area of well 150 immediately adjacent the gas-permeable membrane 160 will be representative of the concentration of those gases in the process medium 150.

Any suitable sealing method can be used to seal the gas-permeable membrane 160 to the channel 180, including compression fits, adhesives, O-rings or other gaskets, or any other sealing method or structure, as well as any combination of such methods and structures. In addition to the seal formed between the gas-permeable membrane 160 and the channel 180, a sealing structure 190 surrounds the open proximal end of the channel 180, and can be adhered or otherwise secured to the wall 110 of the bioreactor 100 to install the gas-permeable well 150 through a hole or port in the wall 110 of the bioreactor 100.

FIG. 1B is a side cross-sectional view schematically illustrating the bioreactor of FIG. 1A, with a dissolved oxygen sensor inserted into the gas-permeable well. By bringing the sensor 130 into close proximity with the gas-permeable membrane 160, an indirect measurement of the amount of dissolved oxygen in the process medium 120 can be obtained, without the need to bring the sensor 130 into actual contact with the process medium 120.

In the embodiment of FIGS. 1A and 1B, the gas-permeable well 150 including the gas-permeable membrane 160 are integral parts of the bioreactor 100 as used. Even if the gas-permeable well 150 does not form a part of the bioreactor 100 as originally manufactured, and is installed at a later point in time, prior to use, the gas-permeable well 150 and the gas-permeable membrane 160 will remain installed and in place from a point in time prior to the sterilization process to a point in time after the process within the bioreactor 100 is complete. The gas-permeable well 150 and gas-permeable membrane 160 represent a potential point of mechanical failure, both because the gas-permeable membrane 160 itself could be ruptured or damaged, and because a seal between gas-permeable membrane 160 and another portion of the gas-permeable well 150 could fail, such as through dislodgement of the gas-permeable membrane 160. The potential for such modes of mechanical failure may place constraints on the conditions to which a bioreactor 100 including a gas-permeable well such as gas-permeable well 150 can be exposed.

In some embodiments, exposure of the gas-permeable membrane 160 to pressure differentials may rupture or dislodge the gas-permeable membrane 160. While a thicker membrane may be less likely to rupture, increasing the overall thickness of the gas-permeable membrane 160 as a whole will reduce the rate at which gas diffuses through the gas-permeable membrane 160, which may increase the time required to obtain an accurate measurement of the process medium. If control of the process within the bioreactor 100 is based in part on the measurement of the process medium, an increase in the time required to obtain an accurate measurement may render the process difficult or impossible to control via feedback from the delayed measurements.

Figure 2B:
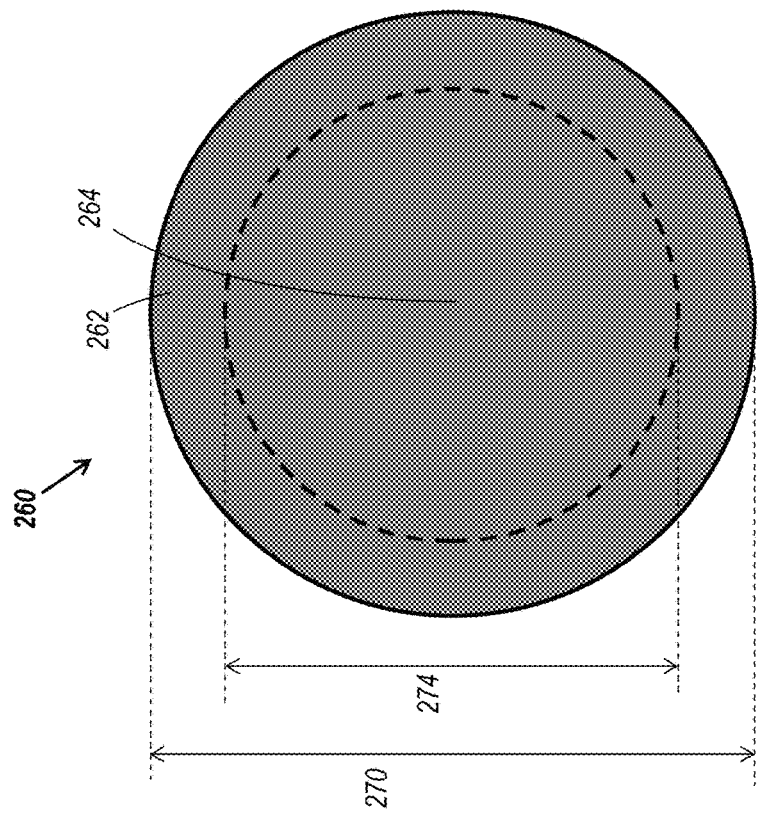
FIGS. 2A and 2B are cross-sectional and top plan views, respectively, of a gas-permeable membrane design with a cross-sectional shape that provides additional reinforcement.
Figure 2A:
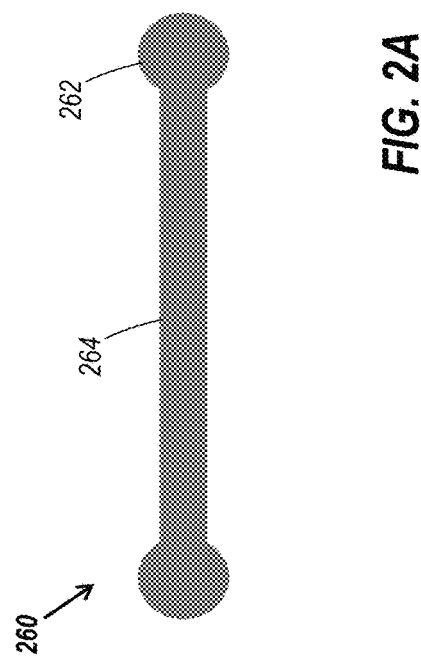

FIGS. 2A and 2B are cross-sectional and top plan views, respectively, of a gas-permeable membrane design with a cross-sectional shape that provides additional reinforcement. FIG. 2A shows a membrane 260 that includes a thicker perimeter region 262 surrounding a thinner central region 264. In the embodiment of FIGS. 2A and 2B, the perimeter region 262 takes the form of a toroidal shape, and may be integrally molded with the thinner, planar, central region 264. In some embodiments, the membrane 260 may be considered to include an integrated O-ring. In some embodiments, the integrated O-ring or similar toroidal structure defining the thicker perimeter region 262 may be formed from the same material as the central region 264, while in other embodiments, the O-ring may be formed from a material that may less permeable to gas and may be more resilient than the material of the integrated O-ring.

By integrating an O-ring or similar feature within the membrane 260, the integrity of the seal between the membrane 260 and a surrounding retaining structure, such as a channel of a gas-permeable well, can be increased. Because the gasket-type structure is integrated into the membrane itself, the number of joints between elements of the well can be reduced in comparison to a well design which utilizes one or more additional gaskets or O-rings adjacent a gas-permeable membrane. This can increase, for example, the reliability of a compression seal between the membrane 260 and an adjacent retaining structure configured to retain the membrane 260 in place.

In addition, the use of a thicker perimeter region 262 can increase the resistance of the membrane 260 to rupture while under load. By increasing the thickness of the perimeter region 262, without necessarily increasing the thickness of the central region 264, the gas-permeable membrane 260 may be reinforced without significantly slowing diffusion of gas through the gas-permeable membrane 260. Because the diameter 274 of the central region 264 is smaller than the overall diameter 270 of the gas-permeable membrane 260, the thinner central region 264 can be resistant to pressure differential than a similarly dimensioned membrane of constant thickness. The thicker perimeter region 262 may also facilitate more secure retention of the membrane within a surrounding retention structure.

Figure 3:
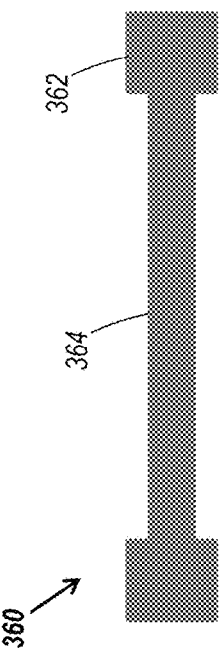
FIG. 3 is a cross-sectional view of another embodiment of a gas-permeable membrane design with an alternate cross-sectional shape that provides additional reinforcement.

In other embodiments, other shapes may be used for the thicker perimeter shape, as well. FIG. 3 is a cross-sectional view of another embodiment of a gas-permeable membrane design with an alternate cross-sectional shape that provides additional reinforcement. Like the membrane 260 of FIG. 2A, the membrane 360 includes a thicker perimeter region 362 surrounding a thinner central region 364. The thicker perimeter region 362 of the membrane 360 is in the form of a flat ring, with substantially rectangular cross-sectional shapes in profile. The generally flat surfaces of the perimeter region 362 provide a larger surface area in contact with adjacent surfaces, which may be helpful when sealing mechanisms such as compression seals and adhesives are used.

In other embodiments, any suitable profile or cross-sectional shape may be used for a thicker perimeter section of a gas-permeable membrane. For example, the profile may be chosen to be complementary with a retaining structure to enable a more secure fit or fluid seal. As another example, although depicted as vertically symmetric in cross-section in the embodiments shown in the figures, the thinner central portion may be located closer to either the inner side or the outer side of the thicker perimeter region.

The use of a reinforced gas-permeable membrane can expand the range of conditions to which a bioreactor containing a gas-permeable membrane can be exposed. As the volume of process media within a bioreactor increases, the hydrostatic pressure on a gas-permeable membrane will increase as well, increasing the likelihood of rupture or dislodgement of the gas-permeable membrane. The use of reinforced gas-permeable membranes such as the reinforced gas-permeable membranes described herein can allow the use of, or increase the reliability of, gas-permeable wells in larger bioreactors. For example, in addition to inclusion of gas-permeable wells in smaller bioreactors, such as 1-liter and 2-liter bioreactors, gas-permeable wells with reinforced membranes can be used in much larger bioreactors, such as 30-liter bioreactors and bioreactors as large as 2,000 liters or larger. In addition, this can enable placement of the gas-permeable wells at lower heights on the wall of a given bioreactor, where hydrostatic pressures may be greater due to the increased volume of process medium above the gas-permeable well.

In addition, the reinforced membrane may provide additional protection against other modes of mechanical failure of the membrane. As the use of a dedicated gas-permeable well allows the insertion and removal of a sensor into the gas-permeable well during the bioreactor process, reinforcement of the membrane protects against accidental puncturing or other rupture of the membrane, which could breach the sterility of the bioreactor and result in a loss of significant time and money.

Figure 4B:
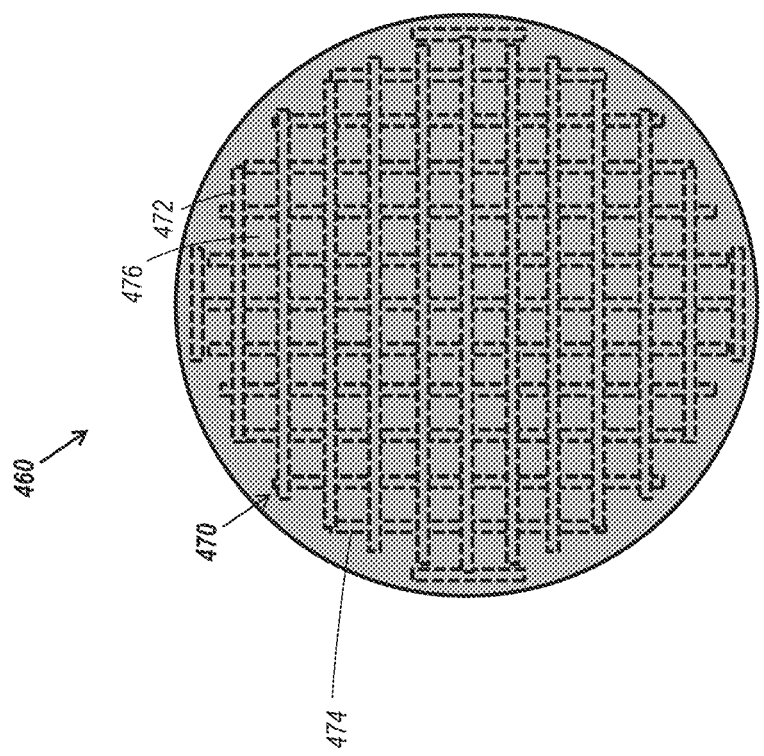
FIGS. 4A and 4B are cross-sectional and top plan views, respectively, of a gas-permeable membrane design with a plurality of integrated reinforcing members.
Figure 4A:
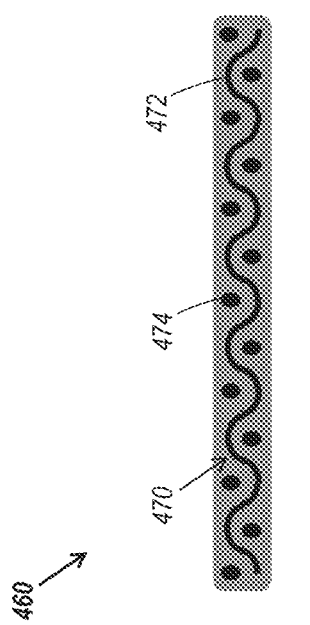

A wide variety of other structures, designs, and configurations can be used to provide additional reinforcement to a gas-permeable membrane. In some embodiments, integrated reinforcing members may be included within the gas-permeable membrane. FIGS. 4A and 4B are cross-sectional and top plan views, respectively, of a gas-permeable membrane design with a plurality of integrated reinforcing members. FIG. 4A shows a membrane 460 that includes a first plurality of reinforcing members 472 extending generally parallel to the plane of the figure and a second plurality of reinforcing members 474 extending generally perpendicular to the plane of the figure. The first plurality of reinforcing members 472 and the second plurality of reinforcing members 474 are interwoven with each other to form a mesh 470, which can best be seen in FIG. 4B.

The mesh 470 provides a reinforcing structure which can be integrated within the gas-permeable membrane material to provide a reinforced gas-permeable membrane. Because the mesh 470 is non-contiguous, and includes a plurality of spaces 476 or apertures between the interwoven first and second pluralities 472 and 474 of reinforcing members forming the mesh 470, the mesh 470 can be formed from a non-permeable material while allowing the reinforced gas-permeable membrane 460 as a whole to be permeable to oxygen and other gases. In some embodiments, the mesh 470 may be formed from a material which is partially or completely gas-impermeable, stainless steel or a similar material, and the mesh 470 may be at least partially encased in a gas-permeable material such as silicone.

Like the reinforcing structures of membranes 260 and 360, the mesh 470 will also reduce the likelihood of mechanical failure of the membrane. In particular, because the mesh 470 extends across at least a central region of the membrane 460, it can provide significant protection against failure of the integrity of the membrane itself, such as rupture due to a pressure differential across the membrane. In contrast to the membranes 260 and 360, which include peripheral reinforcing structures and reduce the size of the thinner central sections, the reinforcing structure of the mesh 470 extends across the entire area of the membrane 460, and increases the overall stiffness of the membrane. By increasing the stiffness of the membrane 460, the deformation of the membrane 460 under load can be reduced, making it less likely that the membrane 460 will undergo rupture or other mechanical failure.

In some embodiments, the internal reinforcing structures can include a structure other than a plurality of discrete reinforcing elements extending across the membrane. For example, a perforated screen or similar structure could be formed by etching apertures into a solid layer of non-permeable material. In some embodiments, this etching could be accomplished via laser etching or another suitable etching process.

A perforated sheet, layer, or screen could provide a reinforcement structure having a lower profile in cross-section than an interwoven mesh, which could decrease the overall thickness of the membrane, and could maintain a smoother outer profile of the membrane when deformed under load. Because discrete reinforcing structures can be embedded within the gas-permeable membrane, or otherwise designed to provide a largely planar profile in contact with the process media, buildup that may interfere with the rapid measurement of conditions within the bioreactor can be minimized or prevented.

In some embodiments, the peripheral reinforcing structures of membranes 260 and 360 may be used in conjunction with the mesh 470 of membrane 460 or a similar structure. FIG. 5A is a cross-sectional view of a reinforced membrane including the peripheral reinforcing structure of FIG. 2A and the reinforcing mesh of FIG. 4. The reinforced membrane 560a includes a thicker perimeter region 562a in the form of an integrated O-ring surrounding a thinner central region 564a. The reinforced membrane also includes a reinforcing mesh 570a extending across the thinner central region 564a and into the thicker perimeter region 562a. The thicker perimeter region 562a may increase the integrity of the seal, while the reinforcing mesh 570a may increase the stiffness of the membrane 560a and reduce the likelihood of rupture.

Figure 5B:
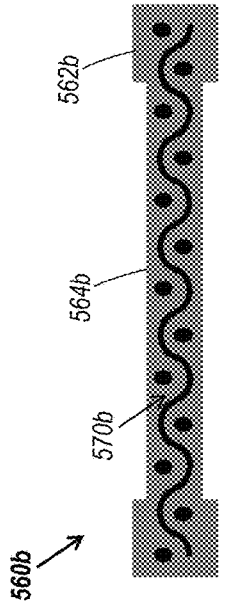
FIG. 5B is a cross-sectional view of a reinforced membrane including the peripheral reinforcing structure of FIG. 3 and the reinforcing mesh of FIG. 4.
Figure 5A:
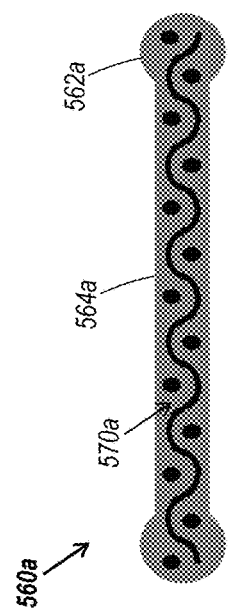
FIG. 5A is a cross-sectional view of a reinforced membrane including the peripheral reinforcing structure of FIG. 2A and the reinforcing mesh of FIG. 4.

Similarly, FIG. 5B is a cross-sectional view of a reinforced membrane including the peripheral reinforcing structure of FIG. 3 and the reinforcing mesh of FIG. 4. The reinforced membrane 560b includes a thicker perimeter region 562b in the form of an integrated flat ring that is thicker than and surrounding a thinner central region 564b. The reinforced membrane also includes a reinforcing mesh 570b extending across the thinner central region 564b and into the thicker perimeter region 562b.

Figure 6B:
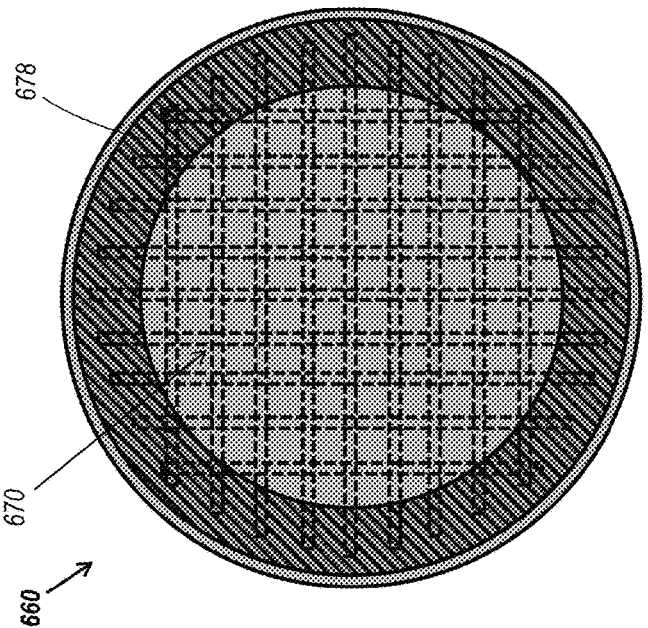
FIG. 6B is a top plan view of the reinforced membrane of FIG. 6A.
Figure 6A:
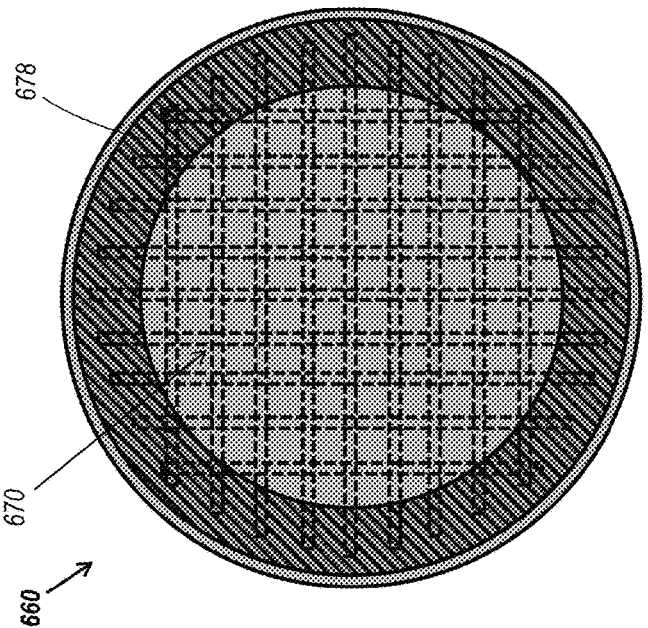
FIG. 6A is a cross-sectional view of a reinforced membrane including a discrete peripheral reinforcing structure internal to the reinforced membrane.

In other embodiments, a peripheral reinforcing structure can include a discrete reinforcing element, rather than being formed only from of a thicker section of gas-permeable material. FIG. 6A is a cross-sectional view of a reinforced membrane including a discrete peripheral reinforcing structure internal to the reinforced membrane. FIG. 6B is a top plan view of the reinforced membrane of FIG. 6A. The reinforced membrane 660 includes an internal reinforcing structure in the form of a mesh 670 that extends across a thinner central portion 664 and into a thicker peripheral structure 662. In addition, the reinforced membrane 660 includes a discrete peripheral reinforcing structure 678 that in the illustrated embodiment is a ring extending around the edge of the reinforced membrane 660. The peripheral reinforcing structure 678 may in some embodiments be securely connected to the mesh 670 by welding, wrapping of the mesh 670 or the individual elements of mesh 670 around the peripheral reinforcing structure 678, or any other suitable means of secure attachment, such that the mesh 670 and peripheral reinforcing structure 678 form a single generally rigid structure.

Like the mesh 670, the peripheral reinforcing structure 678 can be made from stainless steel or another suitable material. The mesh 670 may be connected to and extend across the interior of the peripheral reinforcing structure 678. In the illustrated embodiment, the gas-permeable material completely envelops the mesh 670 and the peripheral reinforcing structure 678. The use of a rigid peripheral reinforcing structure 678 can further increase the stiffness of the reinforced membrane 660, and can support the integrated O-ring or similar gasket feature of the reinforced membrane 660 to increase the integrity of the seal between the reinforced membrane 660 and one or more other components of a reinforced gas-permeable well including the reinforced membrane 660.

Figures 7, 8:
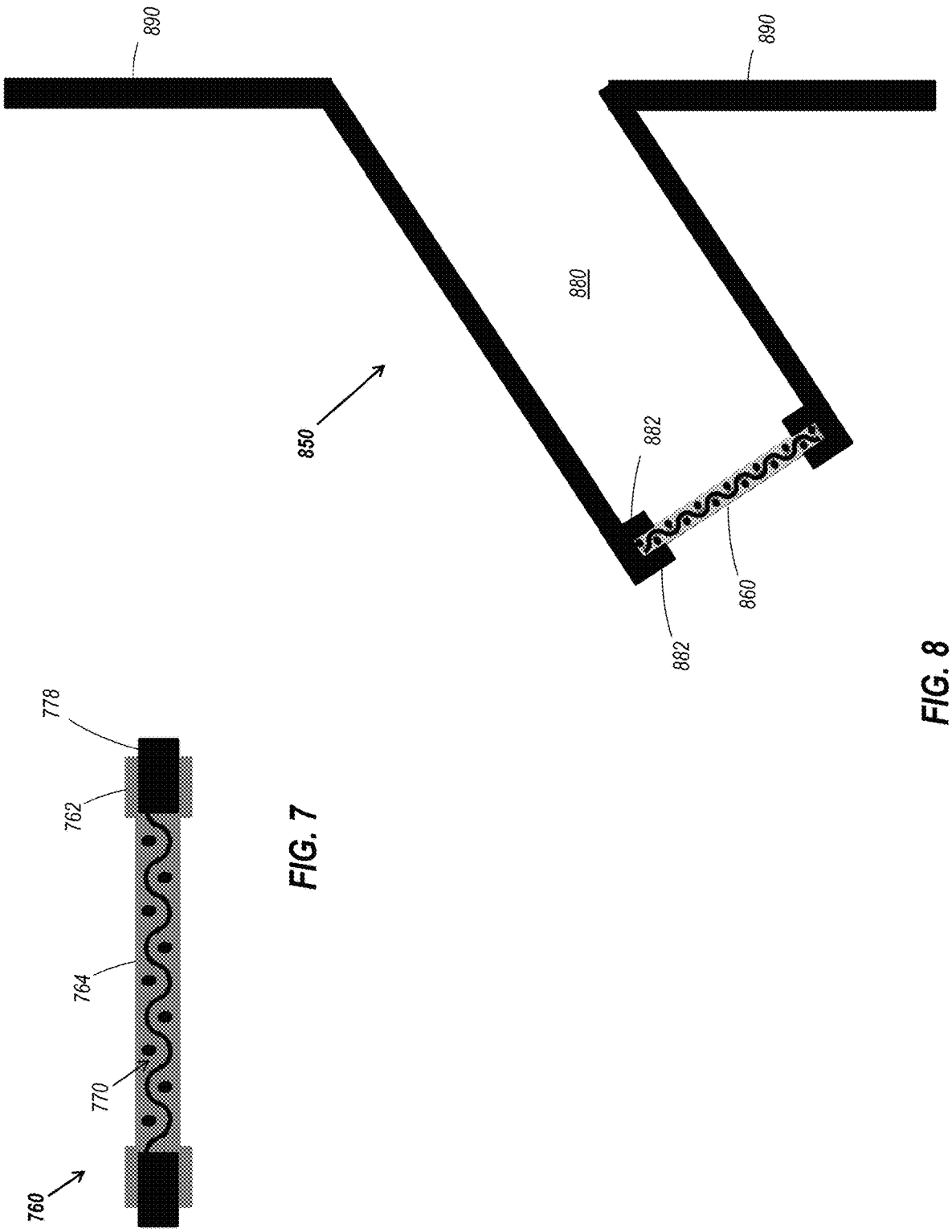
FIG. 7 is a cross-sectional view of a reinforced membrane including a discrete peripheral reinforcing structure at least partially external to the reinforced membrane.
FIG. 8 is a side cross-section of a reinforced gas-permeable well including a reinforced gas-permeable membrane.

FIG. 7 is a cross-sectional view of a reinforced membrane including a discrete peripheral reinforcing structure at least partially external to the reinforced membrane. Like the membrane 660, the membrane 760 includes an internal reinforcing structure in the form of a mesh 770 extending across a thinner central portion 764 and into a thicker peripheral structure 762, as well as a discrete peripheral reinforcing structure 778 in the form of a ring extending around the edge of the reinforced membrane 760. An outer portion of the peripheral reinforcing structure 778 is exposed, extending outside of the gas-permeable material. The partially exposed peripheral reinforcing structure 778 can facilitate certain securement arrangements of the membrane within a retaining structure such as the retaining structures discussed in greater detail below.

Membranes such as the reinforced membranes of FIGS. 2A-7 can be formed by any suitable manufacturing process. In some embodiments, the gas-permeable material can be injection molded, with or without discrete internal reinforcing components. In other embodiments, other suitable manufacturing processes can be used.

A reinforced membrane such as the reinforced membranes of FIGS. 2A-7 can be used in conjunction with a retaining structure to provide a reinforced gas-permeable well which is more resilient than a gas-permeable well including an unreinforced membrane. FIG. 8 is a side cross-section of a reinforced gas-permeable well including a reinforced gas-permeable membrane. In the illustrated embodiment, reinforced gas-permeable well 850 includes a channel 880 having a reinforced membrane 860 at the distal end, and an open proximal end. The membrane 860 forms a fluid-tight seal with the surrounding components of the reinforced gas-permeable well 850. A generally planar sealing structure 890 surrounds the open proximal end of the channel 880.

In the illustrated embodiment, the channel 880 extends along an axis that is oriented at an angle to the normal of the plane defined by the sealing structure 890. This allows the channel 880 to be canted downward when installed, or in any other desired direction, relative to a sidewall of a bioreactor in which the reinforced gas-permeable well 850 is installed. In other embodiments, the channel 880 may be aligned with the normal, or oriented at a larger or smaller angle to the normal.

The reinforced membrane 860 may be retained at the distal end of the channel 880 with a fluid-tight seal formed between the reinforced membrane 860 and the channel 880. The reinforced membrane 860 may be retained there, with a fluid-tight seal formed there, by any suitable retention mechanism or retention structure. In some embodiments, the reinforced membrane may be compression-sealed, press-fit, adhered, welded or otherwise mechanically secured to the channel 880 or an intermediate structure that is itself secured to the channel 880. In some embodiments, flanges or other mechanical stops 882, which may extend inwardly from the walls of channel 880, may be used to secure the reinforced membrane 860 in place, with a seal formed between the reinforced membrane 860 and contacting surfaces of the stops 882 and/or channel 880. Any other suitable retention mechanism, or combination of retention mechanisms, may be used to prevent dislodgement of the reinforced membrane 860 and maintain the integrity of the seal formed by or between the reinforced membrane 860 and one or more adjacent components of the reinforced gas-permeable well 850.

The use of a reinforced membrane such as membrane 660 or 760, having an exposed section of a peripheral ring or other peripheral reinforcing member, may allow for a more robust mechanical connection between the retaining member and the seal. The channel 880 may in some embodiments be integrally formed with the channel 880, such that no discrete retention mechanism is used.

The sealing structure 890 may be used to seal the reinforced gas-permeable well 850 to a portion of a bioreactor wall surrounding a port or other aperture in the bioreactor wall, after insertion of the distal end of the channel 880 through the port or other aperture in the bioreactor wall. The sealing structure 890 of the reinforced gas-permeable well 850 may be brought against and sealed to the wall of the bioreactor to form a fluid-tight and gas-tight seal. By using modular reinforced gas-permeable wells such as reinforced gas-permeable well 850, a single-use bioreactor having a desired configuration can be assembled and sterilized, and provided to an end user.

The channel 880 need not terminate at the sealing structure 890, but may in some embodiments extend through the sealing structure 890 and beyond, to provide additional stability to a DO sensor or other sensor seated therein. In other embodiments, the channel 880 may be substantially smaller or non-existent.

FIG. 9 is a cross-sectional view schematically illustrating an embodiment of a bioreactor having a low-profile reinforced gas-permeable well installed therein, where the reinforced membrane of the gas-permeable well is substantially flush with the wall of the bioreactor. The bioreactor 900 has a low-profile reinforced gas-permeable well 950 installed in one of the walls 910 of the bioreactor 900. The low-profile reinforced gas-permeable well 950 includes a reinforced gas-permeable membrane 960 with a fluid-tight seal formed between the reinforced gas-permeable membrane 960 and at least one other component of the low-profile reinforced gas-permeable well 950. The reinforced gas-permeable well 950 is secured to the wall 910 of the bioreactor 900 by a sealing structure 990 that is generally coplanar with the membrane 960. A retention structure 982, which may extend to one or both sides of the membrane 960, secures the membrane 960 in place and cooperates with the membrane 960 to form a fluid-tight seal.

In such an embodiment, additional support (not shown), which may be external to the bioreactor 900, may be used to support a DO sensor or other sensor brought into contact with or adjacent the membrane 960. Because the reinforced membrane 960 is substantially flush with the bioreactor wall 910 in the embodiment of FIG. 9, the low profile low-profile reinforced gas-permeable well 950 does not reduce the usable interior volume of the bioreactor 900, and does not interfere with other components which may extend into or be inserted into the interior of the bioreactor 900, such as agitators or other sensors.

In some embodiments, the reinforced membranes described above may be used in conjunction with reusable bioreactors, including bioreactors with rigid walls. In such an embodiment, a reinforced gas-permeable well including a reinforced gas-permeable membrane may be built into the rigid bioreactor during the initial construction of the bioreactor. In other embodiments, however, an existing bioreactor can be retrofitted or otherwise modified to include a reinforced gas-permeable well including a gas-permeable membrane.

In some embodiments, the reinforced gas-permeable membrane may be provided as part of a module that can be inserted into or otherwise secured and sealed to an existing access port, tube, well, or other luminal structure within or extending into a reusable bioreactor. Because the gas-permeable membrane is reinforced, the reinforced membrane may remain in place and maintain the integrity of the seal during sterilization processes between bioprocesses or other potentially damaging conditions. In some embodiments, these sterilization processes can involve exposure of the bioreactor to high temperatures and pressures.

In the foregoing description, specific details are given to provide a thorough understanding of the examples. However, it will be understood by one of ordinary skill in the art that the examples may be practiced without these specific details. Certain embodiments that are described separately herein can be combined in a single embodiment, and the features described with reference to a given embodiment also can be implemented in multiple embodiments separately or in any suitable subcombination. In some examples, certain structures and techniques may be shown in greater detail than other structures or techniques to further explain the examples.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A reinforced gas-permeable well for use with a bioreactor, the reinforced gas-permeable well comprising:
   a reinforced gas-permeable membrane, the reinforced gas-permeable membrane comprising:
      a gas-permeable membrane; and
      a gas-impermeable reinforcing structure at least partially embedded within the gas-permeable membrane, the gas-impermeable reinforcing structure including at least one aperture extending therethrough; and
   a retaining structure configured to retain the gas-permeable membrane.

2. The reinforced gas-permeable well of claim 1, wherein the gas-impermeable reinforcing structure includes an interwoven mesh.

3. The reinforced gas-permeable well of claim 1, wherein the gas-impermeable reinforcing structure includes a perforated screen.

4. The reinforced gas-permeable well of claim 1, wherein the gas-impermeable reinforcing structure further includes a ring disposed at the periphery of the gas-impermeable reinforcing structure.

5. The reinforced gas-permeable well of claim 4, wherein the ring is partially embedded within the gas-permeable membrane.

6. The reinforced gas-permeable well of claim 1, wherein the gas-permeable membrane includes silicone.

7. The reinforced gas-permeable well of claim 1, additionally comprising a channel configured to receive a sensor therein, to allow the sensor to be positioned adjacent the reinforced gas-permeable membrane.

8. The reinforced gas-permeable well of claim 1, additionally comprising a sealing structure configured to allow the reinforced gas-permeable well to be installed in a wall of the bioreactor.

9. The reinforced gas-permeable well of claim 8, additionally comprising a channel extending between the sealing structure and the retaining structure, the channel configured to allow a sensor to be positioned adjacent the reinforced gas-permeable membrane.

10. The reinforced gas-permeable well of claim 9, wherein the retaining structure comprises at least one flange extending inwardly from the interior wall of the channel and configured to inhibit translation of the gas-permeable membrane in at least one direction along the channel.

11. The reinforced gas-permeable well of claim 10, wherein the reinforced gas-permeable membrane is oriented at an oblique angle to the sealing structure.

12. The reinforced gas-permeable well of claim 8, additionally comprising a channel extending between the sealing structure and the retaining structure, the channel configured to allow a sensor to be positioned adjacent the reinforced gas-permeable membrane, wherein the reinforced gas-permeable membrane is oriented at an angle to the axis of the channel.

13. A bioreactor comprising the reinforced gas-permeable well of claim 1.

14. The bioreactor of claim 13, wherein the bioreactor comprises a single-use bioreactor having flexible walls.

15. The bioreactor of claim 13, wherein the bioreactor comprises an internal volume of greater than 2 liters.

16. The bioreactor of claim 13, wherein the bioreactor comprises a reusable bioreactor having rigid walls.

17. A reinforced gas-permeable well for use with a bioreactor, the reinforced gas-permeable well comprising:
   a reinforced gas-permeable membrane, the reinforced gas-permeable membrane including a reinforcing structure which decreases the permeability of the gas-permeable membrane in an area adjacent the reinforcing structure; and
   a retaining structure configured to retain the reinforced gas-permeable membrane.

18. The reinforced gas-permeable well of claim 17, wherein the reinforcing structure includes at least one region of increased thickness, and wherein the at least one region of increased thickness extends around the periphery of the reinforced gas-permeable membrane.

19. The reinforced gas-permeable well of claim 18, wherein the at least one region of increased thickness comprises an integrated O-ring or gasket.

20. The reinforced gas-permeable well of claim 17, wherein the reinforcing structure comprises a gas-impermeable reinforcing structure at least partially embedded within the gas-permeable membrane and comprising at least one aperture extending therethrough.

21. The reinforced gas-permeable well of claim 17, wherein the gas-permeable membrane comprises a gas-permeable material which prevents leakage of a process medium therethrough.

22. The reinforced gas-permeable well of claim 17, wherein the gas-permeable membrane forms a fluid-tight seal with surrounding components of the reinforced gas-permeable well.

* * * * *